(12) United States Patent
Lyles

(10) Patent No.: US 6,855,817 B2
(45) Date of Patent: Feb. 15, 2005

(54) MATERIALS AND METHODS FOR BINDING NUCLEIC ACIDS TO SURFACES

(76) Inventor: Mark B. Lyles, 9127 Cap Mountain Dr., San Antonio, TX (US) 78255

(*) Notice: Subject to any disclaimer, the term of this patent is extended or adjusted under 35 U.S.C. 154(b) by 40 days.

(21) Appl. No.: 09/910,697

(22) Filed: Jul. 20, 2001

(65) Prior Publication Data

US 2002/0103350 A1 Aug. 1, 2002

Related U.S. Application Data

(60) Provisional application No. 60/220,096, filed on Jul. 21, 2000.

(51) Int. Cl.[7] ............... C07H 19/00; C07H 19/16
(52) U.S. Cl. ............ 536/25.4; 536/27.21; 536/27.61; 536/27.12
(58) Field of Search ............... 536/25.4, 27.12, 536/27.21, 27.61; 435/91.1

(56) References Cited

U.S. PATENT DOCUMENTS 5,808,041 A * 9/1998 Padhye et al. ............ 536/25.4

FOREIGN PATENT DOCUMENTS

| JP | XP002203983 | 12/1993 | |
| JP | 5-333015 | 12/1993 | ........ G01N/30/48 |
| WO | WO95/06056 | 3/1995 | |
| WO | WO95/34569 | 12/1995 | |

OTHER PUBLICATIONS

Maskos et al., Nucleic Acids Research, vol. 20(7), pp. 1679–1684, 1992.*
Maryanne J. O'Donnell–Maloney, et al., "Microfabrication and Array Technologies for DNA Sequencing and Diagnostics," Genetic Analysis: Biomolecular Engineering, Elsevier Science Publishing, US, vol. 13, No. 6, Dec. 1, 1996, p. 151–152.
Cloarec J. P., et al., "Functionalization of Si/SiO2 Substrates with Homooligonucleotides for a DNA Biosensor," Sensors and Actuators, B, Elsevier Sequoia S.A., Lausanne, CH, vol. 58, No. 1–3, Sep. 21, 1999, pp. 394–398.
Leonard M., "New Packing Materials for Protein Chromatography," Journal of Chromatography B: Biomedical Sciences & Applications, Elsevier Science Publishers, NL, vol. 699, No. 1–2, Oct. 10, 1997, pp. 3–27.

* cited by examiner

*Primary Examiner*—James O. Wilson
*Assistant Examiner*—Howard V. Owens
(74) *Attorney, Agent, or Firm*—Baker Botts L.L.P.

(57) ABSTRACT

Surfaces containing high purity silica (silicon dioxide) exhibit high loading potential for nucleic acids.

Formulations containing nucleic acids and materials which mask the electrostatic interactions between the nucleic acids and surfaces are disclosed. By masking the phosphate charges of the nucleic acids, undesired interactions may be minimized or eliminated, thereby allowing the covalent bonding of the nucleic acids to the surface to proceed. The use of such formulations additionally minimizes nonspecific binding of the nucleic acids to the surface. Examples of materials to be included in such formulations include cations, xanthines, hexoses, purines, arginine, lysine, polyarginine, polylysine, and quaternary ammonium salts.

19 Claims, No Drawings

MATERIALS AND METHODS FOR BINDING NUCLEIC ACIDS TO SURFACES

CROSS REFERENCE TO RELATED APPLICATION

This application claims the benefit under 35 U.S.C. §119 of U.S. Provisional application Ser. No. 60/220,096 filed Jul. 21, 2000.

FIELD OF THE INVENTION

The invention relates to silica surfaces useful for binding nucleic acids, and formulations to improve the binding of nucleic acids to surfaces. In particular, high purity silica (silicon dioxide) surfaces are disclosed. Additionally, nucleic acid formulations containing materials which mask the electrostatic interactions between nucleic acids and surfaces are disclosed.

BACKGROUND OF THE INVENTION

The binding of nucleic acids, especially DNA, to surfaces has been reported many times in the scientific literature. Binding may be accomplished either through nonspecific electrostatic or hydrophobic means, or through formation of covalent bonds to the terminus of the nucleic acid.

Covalent bonding of nucleic acids to surfaces is generally preferred, as it specifically orients the nucleic acids in a given manner. The bonded nucleic acids may be used for hybridization experiments when contacted with other nucleic acids in solution.

Traditionally, glass has been used as the substrate for binding nucleic acids. The glass is heated in order to produce slides or beads. During heating, impurities tend to migrate towards the surface of the material, reducing the surface area available for binding nucleic acids.

Electrostatic interactions between the nucleic acids and the surface result in a fraction of the nucleic acids becoming nonspecifically bound to the surface. This may result in nucleic acids "laying down" or orienting themselves parallel to the surface, rather than being perpendicular to the surface. This orientation reduces or eliminates the ability of the bound nucleic acid to interact with other nucleic acids in solution, and additionally may result in the blockage of other covalent bonding sites on the surface.

There exists a need for improved materials for the preparation of nucleic acids bound to surfaces, and methods to improve the specific covalent bonding of nucleic acids to surfaces.

SUMMARY OF THE INVENTION

Surfaces containing high purity silica (silicon dioxide) exhibit high loading potential for nucleic acids.

Formulations containing nucleic acids and materials which mask the electrostatic interactions between the nucleic acids and surfaces are disclosed. By masking the phosphate charges of the nucleic acids, undesired interactions may be minimized or eliminated, thereby allowing the covalent bonding of the nucleic acids to the surface to proceed. The use of such formulations additionally minimizes nonspecific binding of the nucleic acids to the surface. Examples of materials to be included in such formulations include cations, xanthines, hexoses, purines, arginine, lysine, polyarginine, polylysine, and quaternary ammonium salts. Other materials such as amines may be used if the pH of the formulation is such that the material is positively charged.

DETAILED DESCRIPTION OF THE INVENTION

The prior art materials and formulations have been plagued with two general problems; a) low loading potential of the surfaces; and b) nonspecific binding of nucleic acids to the surface.

A first embodiment of the invention relates to the use of substantially pure silica (silicon dioxide) in surfaces. As there are essentially no impurities in the material, essentially the entire surface of the material is available for binding nucleic acids. Preferably the material is at least about 70% pure, about 80% pure, about 90% pure, about 95% pure, about 96% pure, about 97% pure, about 98% pure, about 99% pure, about 99.5% pure, about 99.9% pure, and ideally about 100% pure by weight. The resulting surface will exhibit higher loading potential for nucleic acids than does conventional glass surfaces. At a microscopic level, the silica surface preferably has a three dimensional structure, and is not planar. An example of a three dimensional structure is an array of silica fibers.

The surface may be generally be any shape, and preferably is macroscopically planar (e.g. a chip or disk) or three dimensional (e.g. a sphere or bead).

The surface properties of the materials may be modified by chemical reactions. Examples include modifying the hydrophobicity or hydrophilicity of the materials.

The surface may be constructed entirely of the substantially pure silica, or may comprise a layer of substantially pure silica mounted on top of a flat surface such as glass or metal. The substantially pure silica may be adhered to the flat surface by an adhesive, applied using a solvent, or cast directly onto the flat surface.

Substantially pure silica may be purchased from a commercial supplier, may be prepared de novo, or may be prepared by purifying silica containing impurities. Methods for treating and purifying silica fibers are taught in U.S. Pat. No. 5,951,295. These methods may be used to purify commercial or prepared silica materials so as to render them substantially pure. The purified silica materials may then be used to prepare the surfaces described herein.

The surface may be used to bind generally any nucleic acids, preferably DNA or RNA, and more preferably DNA. The nucleic acids may be bound to the surface using any acceptable chemical method. Chemical reactions for the covalent bonding of nucleic acids to surfaces containing silica are known in the art.

An additional embodiment of the invention relates to formulations suitable for the binding of nucleic acids to surfaces. Formulations are prepared comprising nucleic acids and a charged material. The charged material preferably is partially or fully cationic. The charged material may generally be any partially or fully positively charged material suitable for interaction with the phosphate groups of nucleic acids. Examples of suitable charged materials include xanthines, hexoses, purines, arginine, lysine, polyarginine, polylysine, and quaternary ammonium salts. The xanthine may generally be any xanthine, and preferably is xanthine, 1,3,7-trimethylxanthine (caffeine), 1,3,9-trimethylxanthine, 1,3-diethyl-7-methylxanthine, 1,3-diethyl-8-phenylxanthine, 1,3-dimethyl-7-(2-hydroxyethyl) xanthine, 1,3-dimethylxanthine-7-acetic acid, 1,3-dipropyl7-methylxanthine, 1,3-dipropyl-8-p-sulfophenylxanthine, 1,7-dimethylxanthine, 1,7-dimethylxanthine (paraxanthine), 1,9-dimethylxanthine, 1-allyl-3,7-dimethyl-8-phenylxanthine, 1-allyl-3,7- dimethyl-8-p-sulfophenylxanthine, 1-butyl-4,5-dihydro-3-ethyl-8-hydroxyxanthine, 1-ethyl-3-isobutylxanthine, 1-methylxanthine, 2,6-dithiopurine, 2'-deoxyinosine, 3,7-dimethyl-1-propargylxanthine, 3,7-dimethylxanthine, 3,8-dimethyl-2-thioxanthine, 3,9-dimethylxanthine, 3-allyl-1-ethyl-8-hydroxyxanthine, 3-cyclopropyl-1-ethyl-8-hydroxyxanthine, 3-ethyl-1-propylxanthine, 3-ethyl-8-hydroxy-1-methylxanthine, 3-isobutyl-1-methylxanthine, 3-isobutyl-1-methylxanthine, 3-isobutyl-1-methylxanthine, 3-isobutyl-1-methylxanthine, 3-methyl-1-(5-oxohexyl)-7-propylxanthine, 3-methyl-8-phenyl-2-thiohypoxanthine, 3-methylxanthine, 3-propylxanthine, 6-thiohypoxanthine, 6-thioxanthine, 7-methylxanthine, 8-(3-carboxypropyl)-1,3-dimethylxanthine, 8-azaxanthine monohydrate, 8-bromo-1,3-diethylxanthine, 8-cyclopentyl-1,3-dimethylxanthine, 8-cyclopentyl-1,3-dipropylxanthine, 8-methoxymethyl-3-isobutyl-1-methylxanthine, 8-methylxanthine, 9-methylxanthine, azaserine-hypoxanthine, hypoxanthine, hypoxanthine 9-beta-d-arabinofuranoside, hypoxanthine 9-d-ribofuranoside (inosine), nicotinamide hypoxanthine dinucleotide phosphate, nicotinamide hypoxanthine dinucleotide phosphate disodium salt, nicotinamide hypoxanthine dinucleotide sodium salt, selenohypoxanthine, or xanthosine. The hexose may generally be any hexose, and preferably is alose, altrose, fructose, galactose, glucose, mannose, sorbose, tagatose, or talose, and more preferably is glucose. The hexose may be the D- or L- isomer. The purine may generally be any purine, and preferably is purine, 6-purinecarbonitrile, 6-purinethiol, or 6-purinethiol riboside. The quaternary ammonium salt may generally be any quaternary ammonium salt, and preferably is benzyltriethyl ammonium chloride (BTEAC), benzyltrimethyl ammonium chloride (BTMAC), benzyltributyl ammonium chloride (BTBAC), tetrabutyl ammonium bromide (TBAB), tetramethyl ammonium chloride (TMAC), tetrabutyl ammonium hydrogensulfate (TBAHS), trioctylmethyl ammonium chloride (TOMAC), N-lauryl pyridinium chloride (PYLC), or N-alkyl- (pyridinium/picolinium) chloride.

The charged material may serve multiple roles in the formulation, e.g. a surfactant may also interact with the phosphate groups of nucleic acids. The charged material may be affected by the pH of the formulation, e.g. amines may be protonated at low pH and deprotonated at high pH. The formulation is preferably a homogeneous mixture, and more preferably is a homogeneous aqueous mixture.

The charged material "masks" the charged phosphate groups of the nucleic acids, reducing or eliminating the potential for nonspecific binding of the nucleic acids to the silica surface by electrostatic attraction. As a result, the amount of nucleic acids nonspecifically binding to the surface is reduced or eliminated.

An additional embodiment of the invention is a method for the binding of nucleic acids to a surface. The method generally involves contacting the above described formulation with a surface containing silica. A particularly preferred embodiment involves contacting the above described formulation with a surface consisting essentially of silica. Any acceptable chemical methodology may be used to covalently bond the nucleic acids to the surface in the presence of the formulation.

The charged material in the formulation reduces nonspecific binding of the nucleic acids to the surface relative to nonspecific binding of nucleic acids to the surface in the absence of the charged material. Preferably, the method substantially eliminates nonspecific binding of the nucleic acids to the surface, and more preferably eliminates nonspecific binding of the nucleic acids to the surface. After the contacting step, the charged material may be removed, e.g. by a washing step.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A method for binding nucleic acids to a surface, the method comprising:
   providing a mixture comprising nucleic acids and a charged material comprising a xanthine compound; and
   contacting the mixture and a surface to produce a bound material, wherein the bound material comprises nucleic acids covalently bonded to the surface.

2. The method of claim 1, wherein the surface consists essentially of silica.

3. The method of claim 1, wherein the surface consists of silica.

4. The method of claim 1, further comprising removing the charged material after the contacting step.

5. The method of claim 1, wherein the nucleic acids comprise DNA.

6. The method of claim 1, wherein the surface is flat.

7. The method of claim 1, wherein the surface is a bead.

8. The method of claim 1, wherein the surface comprises an array of fibers.

9. The method of claim 1, wherein the surface comprises at least 80% pure silicon dioxide.

10. The method of claim 1, wherein the surface comprises at least 90% pure silicon dioxide.

11. The method of claim 1, wherein the surface comprises at least 95% pure silicon dioxide.

12. The method of claim 1, wherein the surface comprises pure silicon dioxide.

13. The method of claim 1, further comprising the xanthine compound selected from the group consisting of: ,3,7-trimethylxanthine (caffeine), 1,3,9-trimethylxanthine, 1,3-diethyl-7-methylxanthine, 1,3-diethyl-8-phenylxanthine, 1,3-dimethyl-7-(2-hydroxyethyl)xanthine, 1,3-dimethylxanthine-7-acetic acid, 1,3-dipropyl-7-methylxanthine, 1,3-dipropyl-8-p-sulfophenylxanthine, 1,7-dimethylxanthine, 1,7-dimethylxanthine (paraxanthine), 1,9-dimethylxanthine, 1-allyl-3,7-dimethyl-8-phenylxanthine, 1-allyl-3,7-dimethyl-8-p-sulfophenylxanthine, 1-butyl-4,5-dihydro-3-ethyl-8-hydroxyxanthine, 1-ethyl-3-isobutylxanthine, 1-methylxanthine, 2,6-dithiopurine, 2'-deoxyinosine, 3,7-dimethyl-1-propargylxanthine, 3,7-dimethylxanthine, 3,8-dimethyl-2-thioxanthine, 3,9-dimethylxanthine, 3-allyl-1-ethyl-8-hydroxyxanthine, 3-cyclopropyl-1-ethyl-8-hydroxyxanthine, 3-ethyl-1-propylxanthine, 3-ethyl-8-hydroxy-1-methylxanthine, 3-isobutyl-1-methylxanthine, 3-isobutyl-1-methylxanthine, 3-isobutyl-1-methylxanthine, 3-isobutyl-1-methylxanthine, 3-methyl-1-(5-oxohexyl)-7-propylxanthine, 3-methyl-8-phenyl-2-thiohypoxanthine, 3-methylxanthine, 3-propylxanthine, 6-thiohypoxanthine, 6-thioxanthine, 7-methylxanthine, 8-(3-carboxypropyl)-1,3-dimethylxanthine, 8-azaxanthine monohydrate, 8-bromo-1,3-diethylxanthine, 8-cyclopentyl-1,3-dimethylxanthine, 8-cyclopentyl-1,3-dipropylxanthine, 8-methoxymethyl-3-isobutyl-1-methylxanthine, 8-methylxanthine, 9-methylxanthine, azaserine-hypoxanthine, hypoxanthine, hypoxanthine 9-beta-d-arabinofuranoside, hypoxanthine 9-d-ribofuranoside (inosine), nicotinamide hypoxanthine dinucleotide phosphate, nicotinamide hypoxanthine dinucleotide phosphate disodium salt, nicotinamide hypoxanthine dinucleotide sodium salt, selenohypoxanthine, xanthosine, and any combination thereof.

14. A method for binding DNA to a surface comprising silica, the method comprising:

providing a mixture comprising DNA and a charged material comprising a xanthine compound; and contacting the mixture and a surface comprising silica to produce a bound material, wherein the bound material comprises DNA covalently bonded to the surface comprising silica.

15. The method of claim 14, further comprising removing the charged material after the contacting step.

16. The method of claim 14, wherein the surface is flat.

17. The method of claim 14, wherein the surface is a bead.

18. The method of claim 14, wherein the surface comprises an array of fibers.

19. The method of claim 14, further comprising the xanthine compound selected from the group consisting of: ,3,7-trimethylxanthine (caffeine), 1,3,9-trimethylxanthine, 1,3-diethyl-7-methylxanthine, 1,3-diethyl-8-phenylxanthine, 1,3-dimethyl-7-(2-hydroxyethyl) xanthine, 1,3-dimethylxanthine-7-acetic acid, 1,3-dipropyl-7-methylxanthine, 1,3-dipropyl-8-p-sulfophenylxanthine, 1,7-dimethylxanthine, 1,7-dimethylxanthine (paraxanthine), 1,9-dimethylxanthine, 1-allyl-3,7-dimethyl-8-phenylxanthine, 1allyl-3,7-dimethyl-8-p-sulfophenylxanthine, 1-butyl-4,5-dihydro-3-ethyl-8-hydroxyxanthine, 1-ethyl-3-isobutylxanthine, 1-methylxanthine, 2,6-dithiopurine, 2'-deoxyinosine, 3,7-dimethyl-1-propargylxanthine, 3,7-dimethylxanthine, 3,8-dimethyl-2-thioxanthine, 3,9-dimethylxanthine, 3-allyl-1-ethyl-8-hydroxyxanthine, 3-cyclopropyl-1-ethyl-8-hydroxyxanthine, 3-ethyl-1-propylxanthine, 3-ethyl-8-hydroxy-1-methylxanthine, 3-isobutyl-1-methylxanthine, 3-isobutyl-1-methylxanthine, 3-isobutyl-1-methylxanthine, 3-isobutyl-1-methylxanthine, 3-methyl-1-(5-oxohexyl)-7-propylxanthine, 3-methyl-8-phenyl-2-thiohypoxanthine, 3-methylxanthine, 3-propylxanthine, 6-thiohypoxanthine, 6-thioxanthine, 7-methylxanthine, 8-(3-carboxypropyl)-1,3-dimethylxanthine, 8-azaxanthine monohydrate, 8-bromo-1,3-diethylxanthine, 8-cyclopentyl-1,3-dimethylxanthine, 8-cyclopentyl-1,3-dipropylxanthine, 8-methoxymethyl-3-isobutyl-1-methylxanthine, 8-methylxanthine, 9-methylxanthine, azaserine-hypoxanthine, hypoxanthine, hypoxanthine 9-beta-d-arabinofuranoside, hypoxanthine 9-d-ribofuranoside (inosine), nicotinamide hypoxanthine dinucleotide phosphate, nicotinamide hypoxanthine dinucleotide phosphate disodium salt, nicotinamide hypoxanthine dinucleotide sodium salt, selenohypoxanthine, xanthosine, and any combination thereof.

* * * * *